(12) United States Patent
Furey et al.

(10) Patent No.: US 12,186,706 B2
(45) Date of Patent: Jan. 7, 2025

(54) PROCESSING SYSTEM FOR MULTIPLE TANGENTIAL FLOW FILTRATION STATIONS IN BIOPROCESSING APPLICATIONS

(71) Applicant: PendoTECH, Princeton, NJ (US)

(72) Inventors: James F. Furey, Plainsboro, NJ (US); Richard Holowczak, South Orange, NJ (US); Jack McMickle, Nazareth, PA (US)

(73) Assignee: PendoTECH, Princeton, NJ (US)

( * ) Notice: Subject to any disclaimer, the term of this patent is extended or adjusted under 35 U.S.C. 154(b) by 0 days.

(21) Appl. No.: 17/710,187

(22) Filed: Mar. 31, 2022

(65) Prior Publication Data

US 2022/0219120 A1    Jul. 14, 2022

Related U.S. Application Data

(62) Division of application No. 16/084,123, filed as application No. PCT/US2017/022130 on Mar. 13, 2017, now abandoned.

(60) Provisional application No. 62/307,894, filed on Mar. 14, 2016.

(51) Int. Cl.
| | |
|---|---|
| *B01D 61/18* | (2006.01) |
| *B01D 61/20* | (2006.01) |
| *B01D 61/22* | (2006.01) |

(52) U.S. Cl.
CPC ............ *B01D 61/18* (2013.01); *B01D 61/20* (2013.01); *B01D 61/22* (2013.01); *B01D 2311/25* (2013.01); *B01D 2313/06* (2013.01); *B01D 2313/16* (2013.01); *B01D 2313/243* (2013.01); *B01D 2315/10* (2013.01); *B01D 2315/16* (2013.01); *B01D 2317/04* (2013.01)

(58) Field of Classification Search
CPC ........ B01D 61/18; B01D 61/20; B01D 61/22; B01D 2311/25; B01D 2313/06; B01D 2313/16; B01D 2313/243; B01D 2313/50; B01D 2315/10; B01D 2315/16; B01D 2317/04; B01D 11/04; B01D 2313/54; B01D 61/08; B01D 2313/20; B01D 2317/06; B01D 2313/56; B01D 2319/04; B01D 35/303; B01D 2313/025; B01D 35/306; C12M 47/12; C02F 2201/007; C02F 9/20; C02F 2201/008
See application file for complete search history.

(56) References Cited

U.S. PATENT DOCUMENTS

| | | |
|---|---|---|
| 6,026,837 A | 2/2000 | Chen |
| 6,544,424 B1 | 4/2003 | Shevitz |
| 7,726,232 B2 | 6/2010 | Furey et al. |
| 7,861,608 B2 | 1/2011 | Furey et al. |

(Continued)

FOREIGN PATENT DOCUMENTS

| | | |
|---|---|---|
| WO | 2015069070 A1 | 5/2015 |
| WO | 2015129520 A1 | 9/2015 |

*Primary Examiner* — Pranav N Patel
(74) *Attorney, Agent, or Firm* — Hoffman & Baron, LLP

(57) ABSTRACT

A multiple tangential flow filtration (TFF) apparatus includes a plurality of tangential flow filtration (TFF) systems, a support frame defining a plurality of stations for supporting individual (TFF) systems and a single controller for controlling the plurality of tangential flow filtration systems. Each of the systems include at least a product vessel, a tangential flow filtration (TFF) filter and a pump for circulating a flow of liquid between said product vessel and said filter.

10 Claims, 8 Drawing Sheets

(56) References Cited

U.S. PATENT DOCUMENTS

| | | |
|---|---|---|
| 7,875,448 B2 | 1/2011 | Furey |
| 7,972,058 B2 | 7/2011 | Furey |
| 8,109,284 B2 | 2/2012 | Furey et al. |
| 8,302,496 B2 | 11/2012 | Furey et al. |
| 8,501,460 B2 | 8/2013 | Furey |
| 2002/0043487 A1 | 4/2002 | Schick |
| 2003/0138349 A1 | 7/2003 | Robinson et al. |
| 2008/0269468 A1 | 10/2008 | Vogel et al. |
| 2010/0206785 A1 | 8/2010 | Beulay et al. |
| 2013/0220477 A1 | 8/2013 | Seeman et al. |
| 2015/0158907 A1 | 6/2015 | Zhou et al. |
| 2016/0289110 A1 | 10/2016 | Oh et al. |
| 2017/0043071 A1 | 2/2017 | Imai |
| 2019/0381459 A1 | 12/2019 | Barch et al. |

PROCESSING SYSTEM FOR MULTIPLE TANGENTIAL FLOW FILTRATION STATIONS IN BIOPROCESSING APPLICATIONS

CROSS-REFERENCE TO RELATED APPLICATIONS

This application is a Divisional Application of U.S. National Phase application Ser. No. 16/084,123 filed Sep. 11, 2018, which claims priority to International Application No. PCT/US2017/022130 filed Mar. 13, 2017, which claims benefit of U.S. Provisional Application No. 62/307,894, the disclosures of which are incorporated herein by reference in their entirety.

BACKGROUND

In the field of biotechnology, there is often a desire to grow cells in culture and a need to separate components in these fluid systems. Such separation has been accomplished by a multitude of methods, including, for example, through centrifugation, chromatography columns, and physical filtering, among many others.

In the case of physical filtering, a filtration device is typically used to selectively remove a percentage of the contents, including any secreted product and cell waste product, of the liquid stream from a bioreactor or during a concentration or diafiltration step in a purification process. A recent technology for biological filtration is commonly known as tangential flow filtration (TFF) or cross flow filtration. TFF systems typically involve the use of hollow fiber or plate/frame membrane technology. Hollow fiber technology utilizes a plurality of relatively thin, fiber tubes that are arranged in parallel to one another. With plate/frame technology, a cartridge consisting of parallel plate membranes is used. In both technologies, a fluid having at least one biological component is passed into a filter (of the tubes or plates), of which the tube or plate membrane wall is designed to allow for the passage of very small components, along with the fluid from the vessel. The fluid and components that are small enough to pass through the filter wall of a specified size is then collected. The fluid that passes through, either with or without the desired biological component, is present in a more pure form relative to the starting fluid.

These filtration systems offer a very effective process selection in many areas of biopharmaceutical processing. This filtration process is made significantly more efficient by the flowing of the liquid medium that occurs along the walls of the hollow fibers or membrane sheets. The flow of that liquid causes the constant removal of material from the inner walls of the filters that would otherwise quickly clog the filter membrane and prevent filtration.

In the development of a new biotechnology manufacturing process, it is preferred to experiment with a range of process parameters to optimize the process to maximize yield and product quality and meet process goals. This in turn, can minimize the cost of goods if a product is scaled up to a large process volume. Some examples of process parameters that are desired to be evaluated in TFF systems are pump flow rates, controlled pressure conditions (transmembrane pressure (TMP)), types of filter, and types of diafiltration buffers. A system that can streamline analysis of the process parameters, impact on yield and product quality is valuable because it can decrease the time required to develop an optimal process by enabling parallel conditions to be tested, at the same time, in an automated fashion.

Accordingly, it would be desirable to provide a TFF system that reduces the impact of potential experimental variance that may be created by testing different conditions over a longer period of time in series. This is especially true when different batches are involved, because the product being tested may vary. It would be further desirable to provide multiple TFF system that can be operated from one main control system, thereby enabling one remote graphical user interface to remotely control the system and to collect all system data for trending and analysis.

SUMMARY

According to an aspect of the invention, a multiple tangential flow filtration (TFF) apparatus is provided. The apparatus includes a plurality of tangential flow filtration (TFF) systems, a support frame defining a plurality of stations for supporting individual TFF systems and a single main controller for controlling the plurality of tangential flow filtration systems. Each of the systems include at least a product vessel, a tangential flow filtration (TFF) filter and a pump for circulating a flow of liquid between said product vessel and said filter.

In a preferred embodiment, the support frame defines at least one interior chamber for containing a pump of each tangential flow system. The support frame further preferably supports each tangential flow filtration (TFF) system in a vertical orientation with respect to a direction of gravity.

Each tangential flow filtration system further preferably includes a product container, and the support frame further preferably includes a plurality of hangers, wherein each hanger hangs a product container of a respective system above its product vessel, whereby a product liquid is fed by gravity to the product vessel.

Each tangential flow filtration system further preferably includes a buffer container hung from a respective one of the plurality of hangers. The product container and the buffer container are in fluid communication with the product vessel of each system via tubing. A buffer selection valve is fluidly connected to the tubing between the buffer container and the product vessel. The buffer selection valve is electrically connected to the main controller for controlling a flow of a buffer liquid from the buffer container to the product vessel. For example, the buffer selection valve enables a flow of buffer fluid during certain processing steps, such as diafiltration.

Each tangential flow filtration system further preferably includes an air-in-tube detector fluidly connected to the tubing between the product container and the product vessel. The air-in-tube detector is electrically connected to the controller for sending an electrical signal to the controller when air is detected within the tubing.

Each tangential flow filtration system further preferably includes a diafiltration valve fluidly connected to the tubing between the product and/or buffer container and the product vessel. The diafiltration valve is electrically connected to the controller for controlling a flow of liquid from the product and/or buffer container to the product vessel.

Each tangential flow filtration system further preferably includes at least one adjustable level sensor disposed adjacent the product vessel for detecting a liquid level in the product vessel. The adjustable level sensor is electrically connected to the controller for sending an electrical signal to the controller upon detecting the desired level in the product vessel. The sensor can be supported on an adjustable bracket assembly attached to the support frame for adjusting a height of the level sensor with respect to the product vessel. The adjustable bracket assembly preferably includes a longitudinal rail fixed to the support frame in a vertical orientation, a carriage slidably mounted on the rail and a clamping device for securing the carriage at a desired height along the rail.

Each tangential flow filtration system further preferably includes a filtrate vessel connected to an output of the tangential flow filtration filter and a filtrate scale supporting the filtration vessel for measuring an amount of fluid in the filtrate vessel. The filtrate scale is electrically connected to the controller for sending an electrical measurement signal to the controller.

Each tangential flow filtration system further preferably includes a throttle valve fluidly connected to an output of the tangential flow filtration filter. The throttle valve is electrically connected to the controller for controlling average transmembrane fluid pressure in the tangential flow filtration filter. It is also possible to control the system based on an inlet pressure or retentate pressure set point. In this case, software would be provided to allow input of a pressure value and for the comparison of the set point to make the correct valve adjustments.

In either case, an inlet pressure sensor is fluidly connected to an inlet of the tangential flow filtration filter and a retentate pressure sensor is fluidly connected to a first outlet of the tangential flow filtration filter for measuring an outlet pressure. The inlet and retentate pressure sensors are electrically connected to the controller for sending pressure signals to the controller to control the throttle valve. In addition, a filtrate (or permeate) pressure sensor can be fluidly connected to a second outlet of the tangential flow filtration filter for measuring a pressure of fluid filtered out of the filter.

Each tangential flow filtration system further preferably includes a stir plate supporting the product vessel. The stir plate has a stir mechanism for stirring fluid in the product vessel.

In another aspect of the present invention, a method for performing multiple tangential flow filtration (TFF) processes is provided. The method includes supporting a plurality of tangential flow filtration (TFF) systems, as described above, on a single support frame, and controlling the plurality of tangential flow filtration systems with a single electrical controller.

The method may also include the steps of detecting air in tubing fluidly connecting a product container to the product vessel and closing at least one of a buffer selection valve, fluidly connected to a buffer container and the product vessel, or a diafiltration valve, fluidly connected between the product container and the product vessel, upon the detection of air in the tubing.

The method may also include the steps of detecting a level of liquid in the product vessel with at least one level sensor, and closing a diafiltration valve, fluidly connected between the product container and the product vessel, upon detection of a desired level of liquid in the product vessel.

The method may also include the steps of detecting an amount of liquid in a filtrate vessel fluidly connected to an outlet of the tangential flow filtration filter with a filtrate scale, and closing at least one of a buffer selection valve, fluidly connected to a buffer container and the product vessel, or a diafiltration valve, fluidly connected between the product or buffer container and the product vessel, upon detection of a desired level of liquid in the filtrate vessel (when the process reaches a desired end point). Alternatively, a filtrate flow meter can be used in place of the filtrate scale to measure a flow rate of the filtrate and estimate total flow.

The method may also include the steps of controlling average transmembrane fluid pressure in the tangential flow filtration filter with a throttle valve fluidly connected to an output of the tangential flow filtration filter, wherein the throttle valve applies a back pressure in the filter. In the alternative, the throttle valve can be activated to apply a back pressure upon the detection of an inlet pressure or retentate pressure set point.

Features of the disclosure will become apparent from the following detailed description considered in conjunction with the accompanying drawings. It is to be understood, however, that the drawings are designed as an illustration only and not as a definition of the limits of this disclosure.

DETAILED DESCRIPTION

Figure 1:
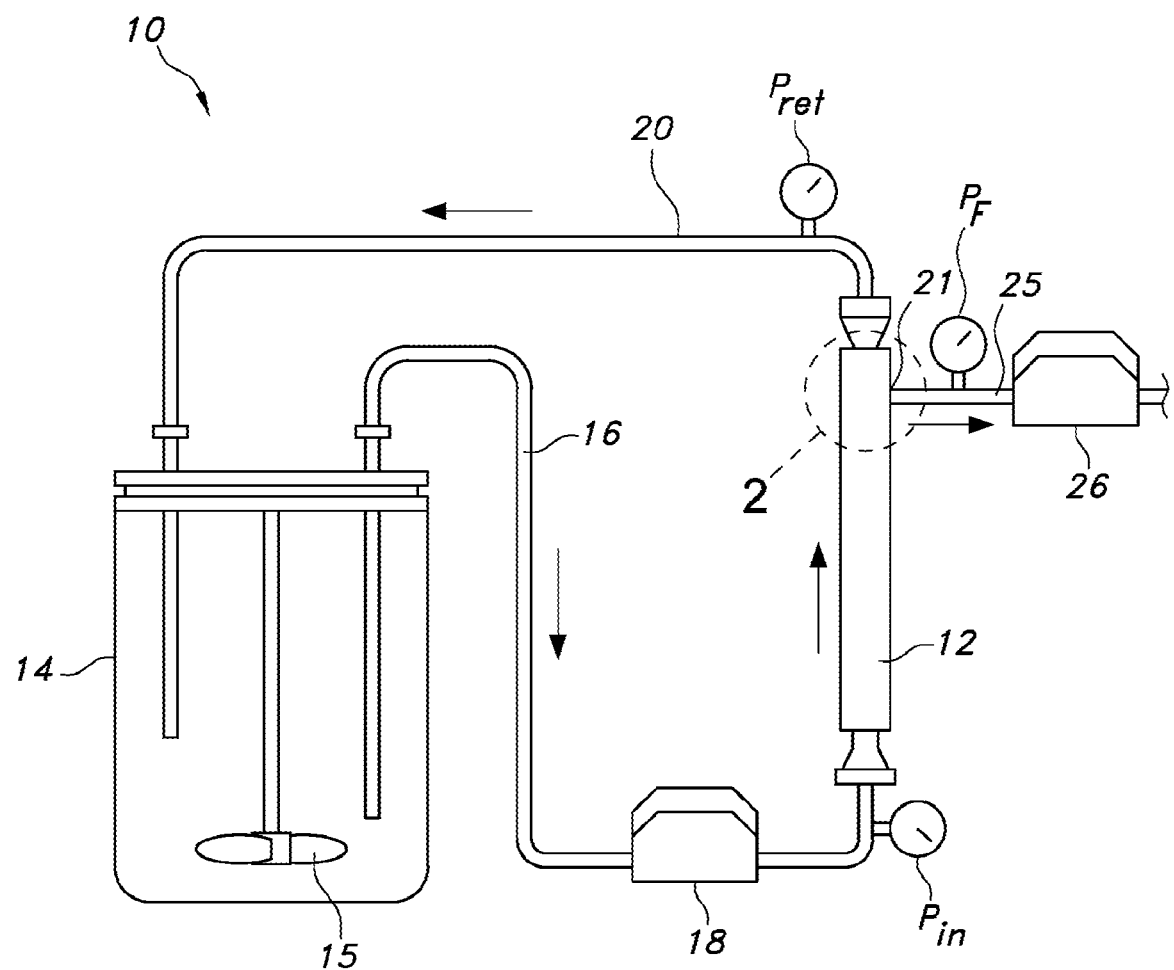
FIG. 1 is a schematic diagram of a typical tangential flow filtration (TFF) system of the prior art.

A typical tangential flow filtration (TFF) or cross flow filtration system 10 using a filter module 12 is represented in FIG. 1. As discussed above, the filter module 12 can utilize hollow fiber or plate and frame cassette flat sheet technology. A container 14 is provided to hold a fluid to be purified to isolate a product of interest based primarily on a size separation process. An impeller 15 may be incorporated within the container 14 to allow for mixing. A container outlet tube 16 is provided to allow fluid to be withdrawn from the container 14. A circulation pump 18 is used to pull the fluid out of the container and force it through the filter 12, as is indicated by the fluid directional flow arrows.

Figure 2:
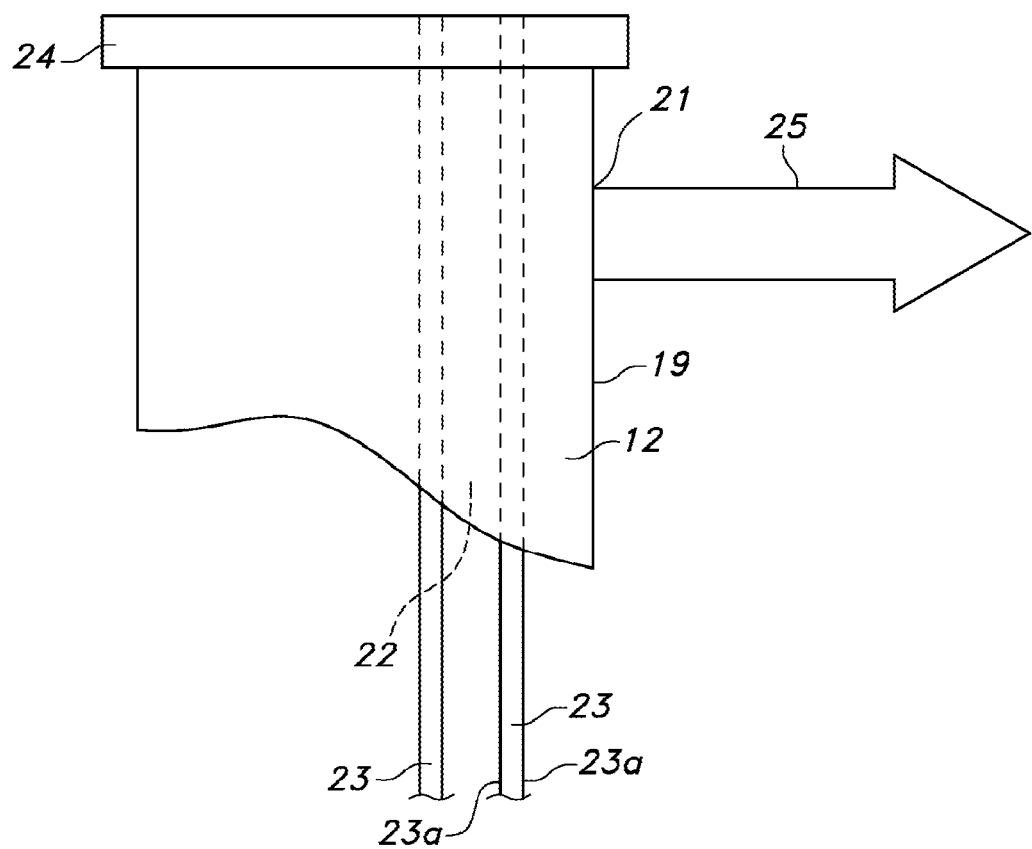
FIG. 2 is an enlarged isolated view of the tangential flow filter shown in FIG. 1.
Figure 2A:
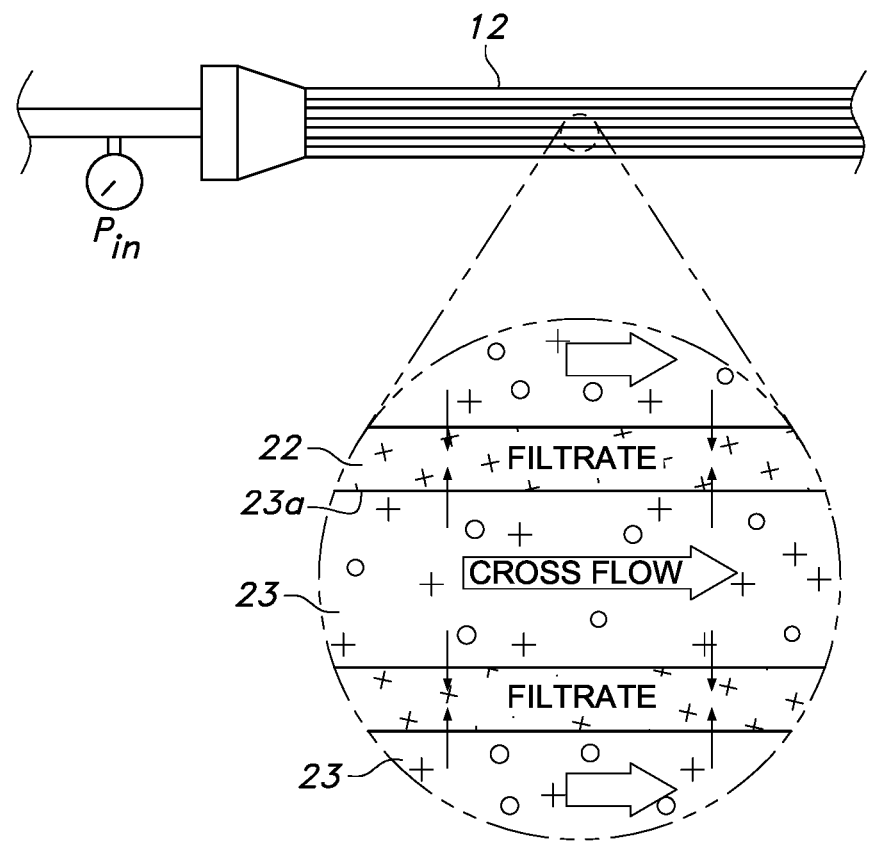
FIG. 2a is another enlarged isolated view of the tangential flow filter shown in FIG. 1.

As shown in further detail in FIG. 2 and FIG. 2a, the filter 12 can be a hollow fiber filter containing numerous hollow fibers 23, or the filter can be a plate filter containing an arrangement of parallel membrane walls 23a. In a hollow fiber filter, the liquid flows into the inner cross section of the individual fibers 23. In a plate filter, the fluid flows between adjacent membrane walls 23a. In either case, the filters can be disposable units having a plastic housing, or can be units having a permanent housing into which disposable filter cartridges are inserted.

The pressurized media ("retentate") is forced out of the filter 12 and into a return tube 20. Filtered fluid is collected through a filtrate collection port 21 on the filter housing 19 and passed through a filtrate collection tube 25. A pump 26 can optionally be included to control the flow of filtrate from the filter 12.

FIG. 2 and FIG. 2a show cutaway views of the filter 12. In the case of a fiber filter, the filter housing 19 contains a plurality of cylindrical, hollow fibers 23 disposed in parallel in a bundle that extends from a first end 24 to a second end (not shown). For clarity, only two hollow fibers 23 are shown in FIG. 2 and three fibers 23 are shown in FIG. 2a. In the case of a plate filter, the filter housing 19 contains a plurality of parallel membrane walls 23a that extend from a first end 24 to a second end (not shown). For clarity, only four membrane walls 23a are shown in FIG. 2 and FIG. 2a.

The hollow fibers 23 or walls 23a are sealed at the first end 24 and the second end in such a manner so that filtrate spaces 22 are defined within the filter housing 19 that are bound by the internal surface of the filter housing 19. In the case of fiber filters, these spaces 22 are defined between individual hollow fibers 23. In the case of plate filters, the spaces 22 are defined between pairs of plate membranes 23a. In either case, sealant material (not shown) is used to seal the first end 24 and the second end around the ends of the filter fibers/plates.

As is well known in the art, if a liquid is forced under pressure through the lumens of the hollow fibers 23, or between alternating pairs of plate membranes 23a, most of the liquid will pass through the filter 12 and out of the second end of the filter 12. Some of the liquid, however, and any components present in the liquid that are smaller than the pore size of the outer surface of the hollow fibers 23 or the walls 23a, will pass or "permeate" through the fibers or walls and accumulate in the spaces 22 defined within the filter housing 19. The fluid and components that collect in the space 22 is known as the filtrate. The filtrate is removed from the filter 12 through the port 21 in the filter housing 19 and through the filtrate tube 25. The pump 26 can be installed in the filtrate tube 25 line to control the flow of filtrate from the filter 12 and to prevent rapid filter fouling.

The feed pressure ($P_{LN}$) is higher than the retentate pressure in ($P_{REY}$) because of the pressure drop as liquid flows through the narrow fibers 23 and returns to the vessel 14. There is also a pressure drop across the fiber wall and the filtrate pressure can be optionally measured at Pf if not at or near to atmospheric pressure. Monitoring of these pressures is critical to measure process performance and for process control.

The longitudinal cross flow rate through the filter 12 is orders of magnitude above the filtrate flow rate and it is this phenomenon that prevents a membrane filter from clogging from material that would rapidly clog a membrane filter operating in "normal flow" filtration. In flat sheet devices, even though the geometry of the device is different, the operation of the process is similar.

In a TFF concentration process, as filtrate is removed, the vessel contents are concentrated. In a diafiltration process (washing to change the solvent environment), liquid or buffer is added to the product vessel to maintain a relatively constant volume as filtrate removal occurs. Depending on the process, the desired product is retained in the vessel by the filter (as in protein concentration processes), or the product may be in the filtrate (as in separation of cells from a secreted product where the cells are retained in the vessel by the filter).

Figure 3:
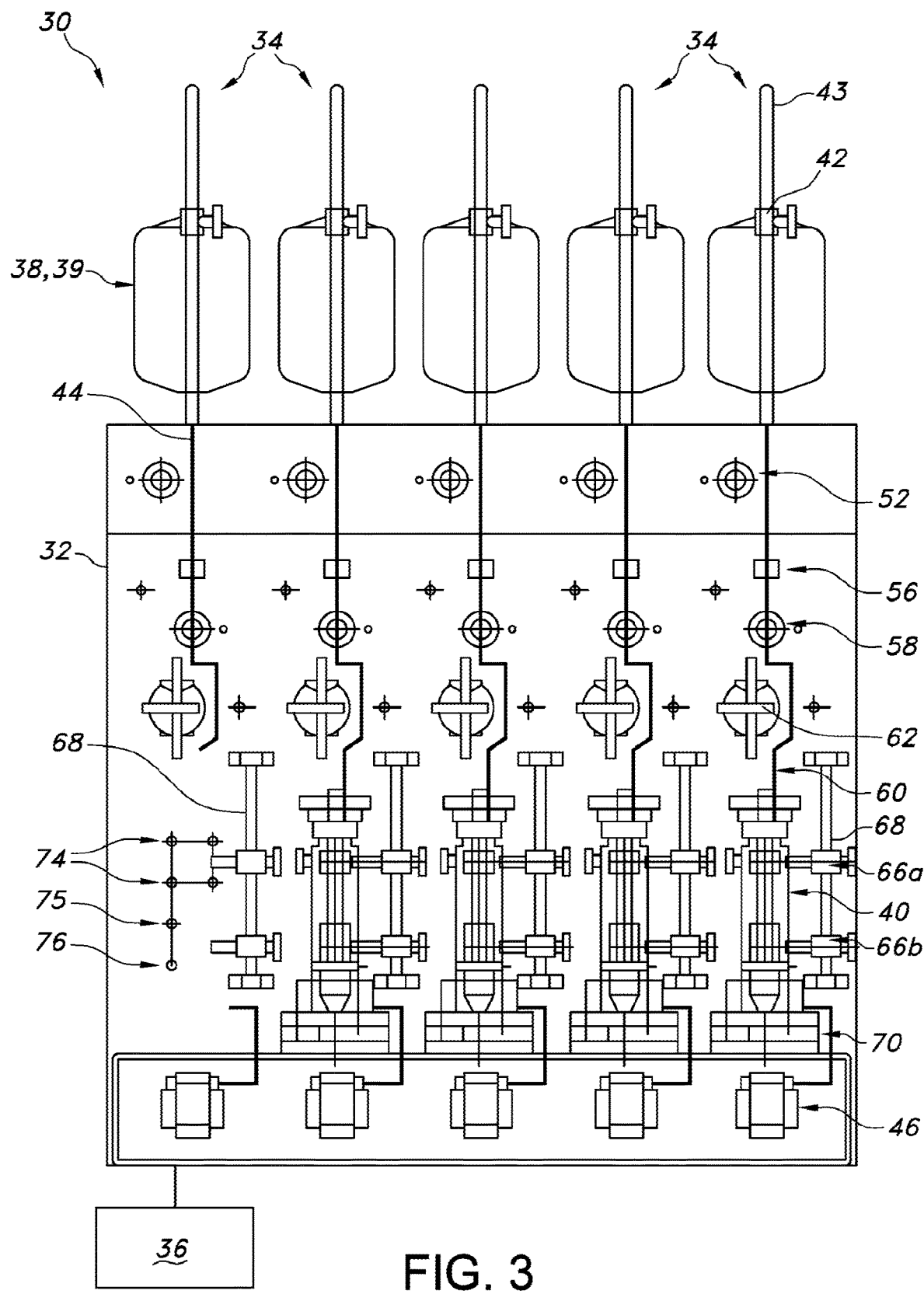
FIG. 3 shows the multiple tangential flow filtration (TFF) system according to one aspect of the present invention.
Figure 4:
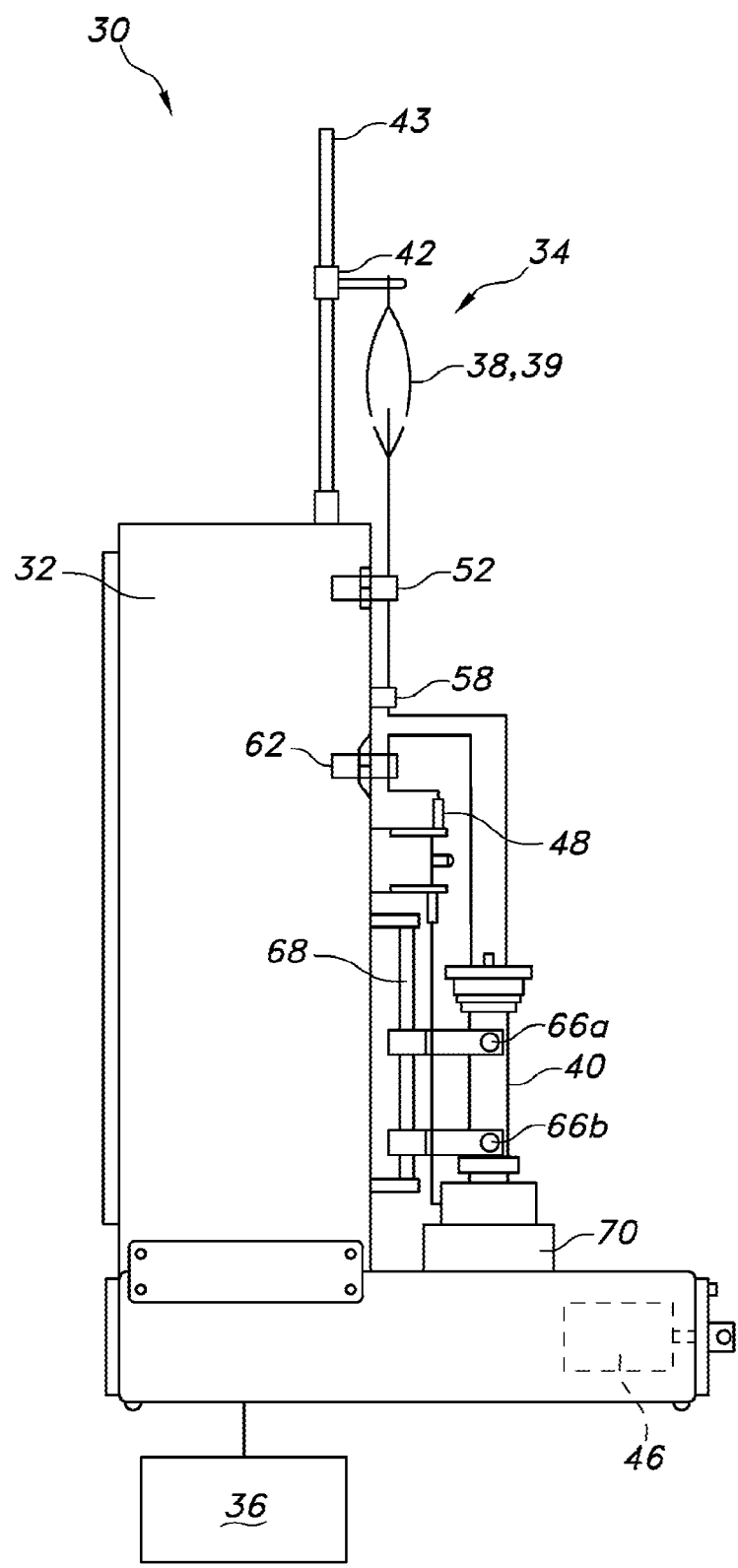
FIG. 4 is a side view of the multiple tangential flow filtration (TFF) system shown in FIG. 3.

Turning now to FIGS. 3 and 4, in one aspect of the present invention, an apparatus 30 enabling simultaneous multiple filtration processes is provided. The apparatus 30 generally includes a single support frame 32 supporting multiple filtration systems 34 in a vertical orientation in order to conserve space. The support frame 32 can be constructed from multiple structural components. For example, a horizontal base box can be attached to a vertical box frame to form the L-shaped support frame 32 shown in FIG. 4. Also, additional separate boxes to house one or more of the valves discussed below can also be attached to the vertical box frame or the base box.

In any event, the system 30 further includes a single main control system 36 for automated simultaneous control of the multiple vertical systems 34. The control system 36 can also be supported by the support frame 32, or it can be provided separate. The control system 36 can be hard wired to the various components of the system, or it can be adapted for wireless communication.

Figure 5:
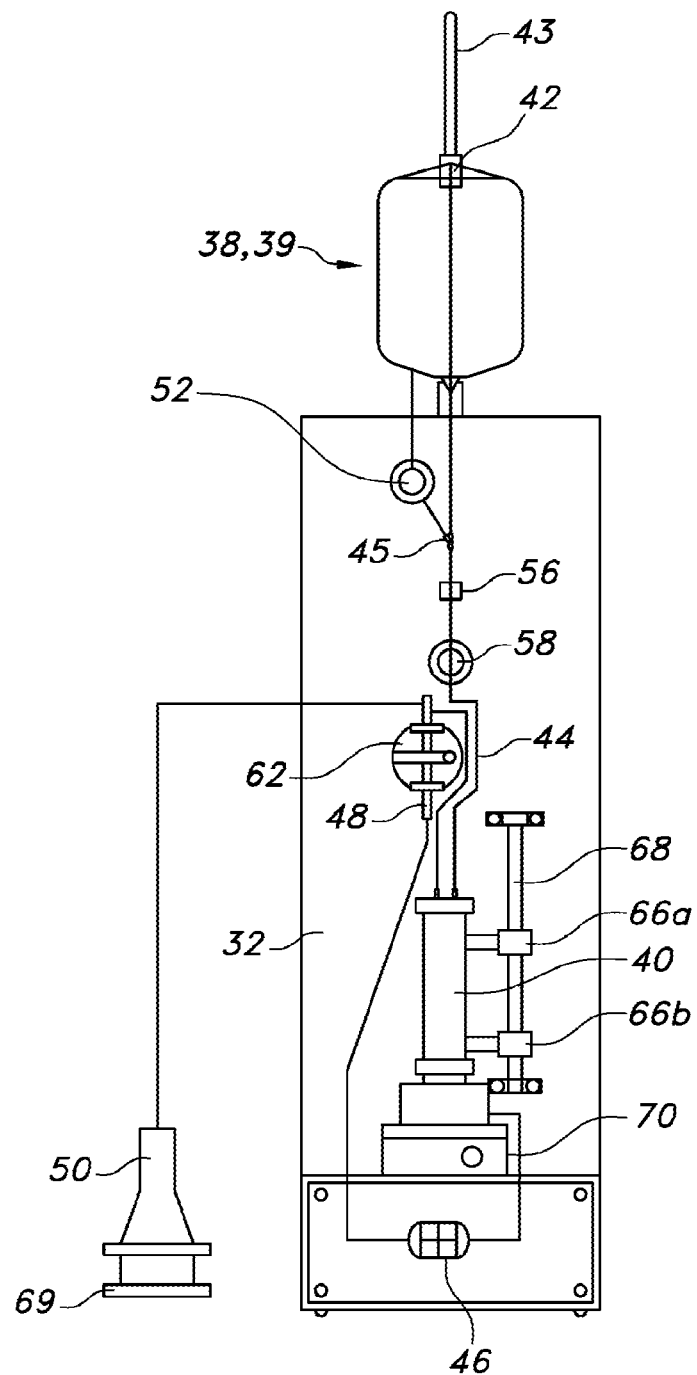
FIG. 5 shows one of the tangential flow filtration (TFF) systems of FIGS. 3 and 4 in isolation.
Figure 6:
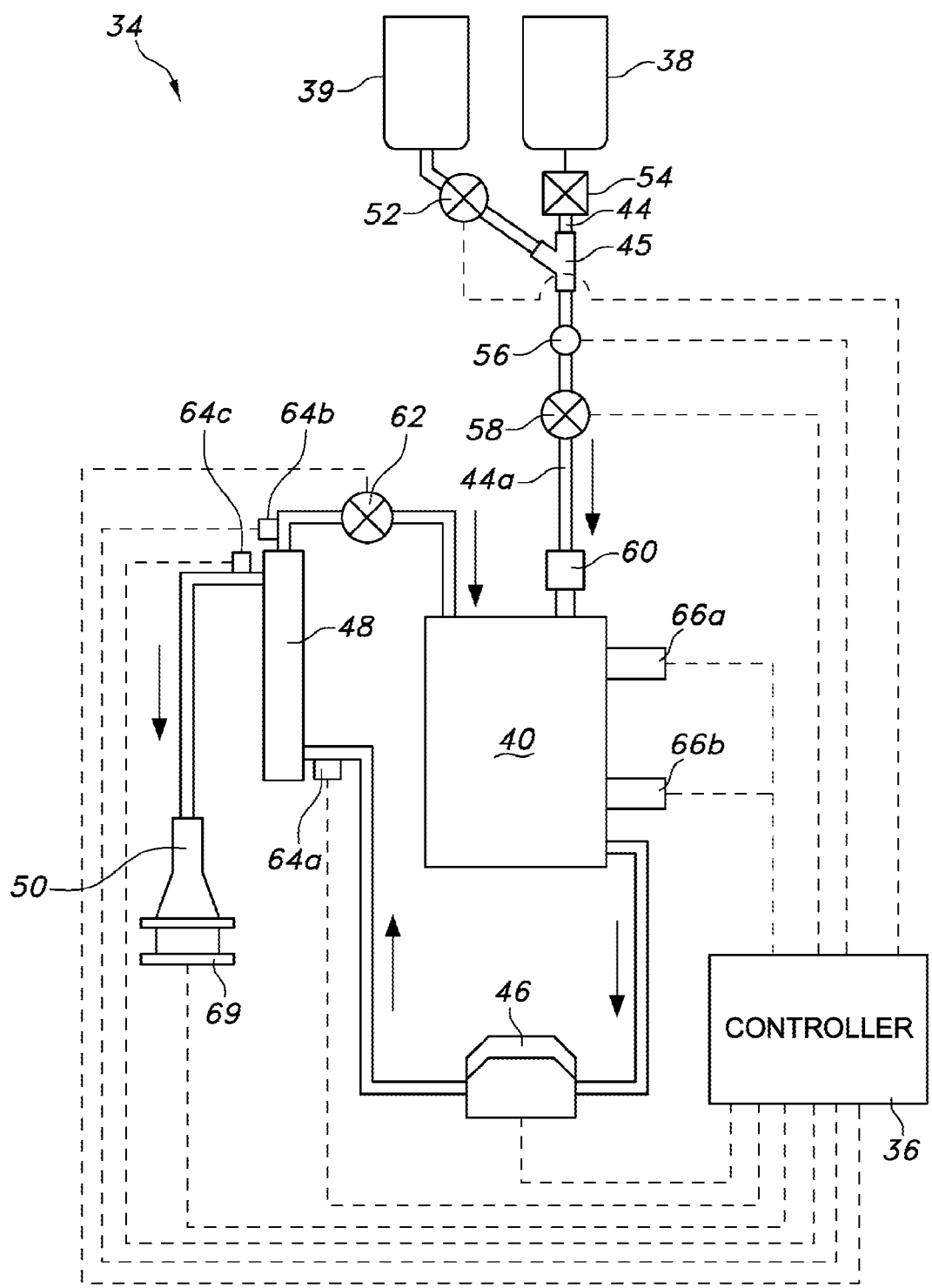
FIG. 6 shows one of the tangential flow filtration (TFF) systems of FIGS. 3 and 4 in schematic form.

Referring additionally to FIG. 5, which shows one of the multiple systems 34 in isolation, and FIG. 6, which shows the system of FIG. 5 in schematic form. Each system 34 includes a product container 38, containing the product to be processed, and a buffer container 39, containing a liquid to be added to the product vessel 40 in order to change the solvent environment of the product during a diafiltration process. In an alternative embodiment, a single buffer container 39 can be connected to multiple systems 34.

Both product and buffer containers 38, 39 are supported by the base frame 32 above the product vessel so that the liquid product and the liquid buffer are fed to the product vessel 40 by gravity. A hanger 42 or other suitable bracket may be provided to connect the product and buffer containers to the frame 32 in a suspended fashion. The hanger 42 can be adjustably connected to a vertical pole 43 mounted to the support frame 32 so that various sizes of containers 38, 39 can be accommodated.

Tubing 44, such as silicone tubing or other suitable thermoplastic tubing, connects the product and buffer containers 38, 39 to the product vessel 40. A Y-connector 45 connects individual tubes 44 from the product and buffer containers 38, 39 to a single inlet tube 44a feeding the product vessel. As will be discussed in further detail, tubing 44 is also provided to provide a fluid conduit between the product vessel 40, a circulating pump 46, a tangential flow filter 48 and a filtrate vessel 50. However, a number of additional components are also provided to enhance the filtration process according to the present invention.

Specifically, a buffer selection valve 52 is connected in the tubing line 44 between the buffer container 39 and the Y-connector 45 leading to the inlet tube 44a. The buffer selection valve 52 is electrically connected to the controller 36. Upon receiving a signal from the controller, via a software program or manual command, the buffer selection valve can be opened or closed as desired, to control the flow of the buffer liquid to the product vessel 40.

Installed within the tubing 44 between the product container 38 and the Y-connector 45 is a manual check valve 54 (not shown in FIGS. 3, 4 and 5). The check valve 54 ensures one-way fluid flow from the product container 38 to the product vessel 40. The check valve 54 also prevents fluid from the buffer container 39 from flowing into the product container 38 should there be a flow stoppage downstream of the Y-connector 45.

Downstream of the Y-connector 45 is an air-in-tube detector 56. The air-in-tube detector 56 is an electrical sensor that detects the presence of air in the tubing 44, such as when fluid is no longer flowing from the product container 38 when the product container is empty. The air-in-tube detector 56 is also electrically connected to the controller 36 for sending a signal to the controller upon detection of air in the line 44. As will be discussed in further detail below, such signal can be used to stop the filtration process entirely or to open the buffer selection valve 52 to feed buffer liquid into the process in a successive step.

Following the air-in-tube detector 56 is a diafiltration valve 58, which is also electrically connected to the controller 36. The diafiltration valve 58 controls the overall flow of fluid (product and/or buffer) to the product vessel 40 based on signals from the controller. As will be discussed in further detail below, such signals from the controller 36 may be in response to the sensing components, such as the liquid level sensors 66a and 66b, of the system, or may be as the result of a software program in the controller.

A flow restrictor 60 is also preferably installed in the inlet tube 44a leading to the product vessel 40. The flow restrictor 60 is an additional safety feature for controlling the rate of flow of liquid to the product vessel 40.

Fluid fed to the product vessel 40 is circulated from the product vessel by a circulating pump 46 through a tangential flow filter 48 and back to the product vessel via plastic tubing 44. The filtrate that is removed from the fluid flow by the filter 48 is fed to a filtrate vessel 50.

However, unlike conventional TFF systems, a controllable throttle valve 62 is provided between the outlet of the filter 48 and the product vessel 40 for providing an adjustable back pressure within the filter. Preferably, the throttle valve 62 does not invade the actual space of the fluid flow. Instead, the throttle valve 62 is designed to reduce the inner diameter of the tubing 44 by a closing action to thereby restrict the flow of fluid through the tubing. By restricting the flow in this manner, a back pressure is applied in the filter 48 that increases the filter efficiency by forcing liquid through the membrane or tubes of the filter.

The back pressure within the filter can be detected by inlet and retentate pressure sensors 64a, 64b connected to the respective inlet and outlet of the filter 48. A filter pressure sensor 64c can also be provided to optionally measure the pressure of the liquid leaving the filter. These sensors 64a, 64b, 64c are also connected to the controller 36, which in turn regulates the throttle valve 62 depending on the pressure readings received from the sensors.

According to another aspect of the present invention, liquid level sensors 66a, 66b are provided at the product vessel 40 for providing another flow control feature of the system. Specifically, an upper liquid level sensor 66a is supported on the base frame 32 by an adjustable bracket assembly 68 for reading an upper limit of the liquid level in the product container 40. Similarly, a lower liquid level sensor is also supported on the base frame 32 by the same adjustable bracket assembly 68 for reading a lower limit of the liquid level in the product container.

The sensors 66a, 66b themselves can be conventional (e.g., optical, capacitive, ultrasonic, radar) sensors that are positioned in close proximity to the product vessel 40 for reading the level of the fluid in the vessel. The sensors 66a, 66b are further electrically connected to the controller for sending signals to the controller when the upper or lower liquid level limit has been reached.

The system 30 further preferably includes a filtrate scale 69 supported on the base frame 32 for weighing the amount of filtrate collected in the filtrate vessel 50. The filtrate scale 69 is electrically connected to the controller 36 for sending a signal to the controller once a desired amount of filtrate has been collected within the filtrate vessel 50. As will be discussed in further detail below, this signal can be used to halt the process or to open the diafiltration valve to add more fluid to the process.

The system 30 may also include a stir plate 70 supported on the base frame 32 for supporting the product vessel 40. The stir plate 70 can be a conventional device used in laboratory environments for stirring the contents of fluid within a vessel.

In another possible embodiment, as an alternative to the circulating pump 46 that is panel mounted and could be of a variety of pump types such as diaphragm, piston or peristaltic, would an electrical connector panel mounted to enable connection of external remote controllable console style pumps which would enable the ability to quickly change the pump used with the system.

It can be appreciated that the base frame 32 is designed to accommodate all of the components of the system, as well as all of the necessary electrical connections. In this regard, the base frame 32 may include conventional plug-in electrical connectors on the exterior surface of the frame with electrical wiring contained within the frame. For example, connectors 74 for the filter pressure sensors 64a, 64b are installed on the surface of the frame adjacent the filter sensors. Similarly, stir plate connectors 75 and filtrate scale connectors 76 are also installed on the frame at convenient locations.

The frame 32 is also designed to support multiple filtration systems 34. Specifically, brackets and other hardware are provided in a parallel alignment for connection of, for example, the buffer selection valve 52, the diafiltration valve 58 and the throttle valve 62 of each system 34.

Figure 7:
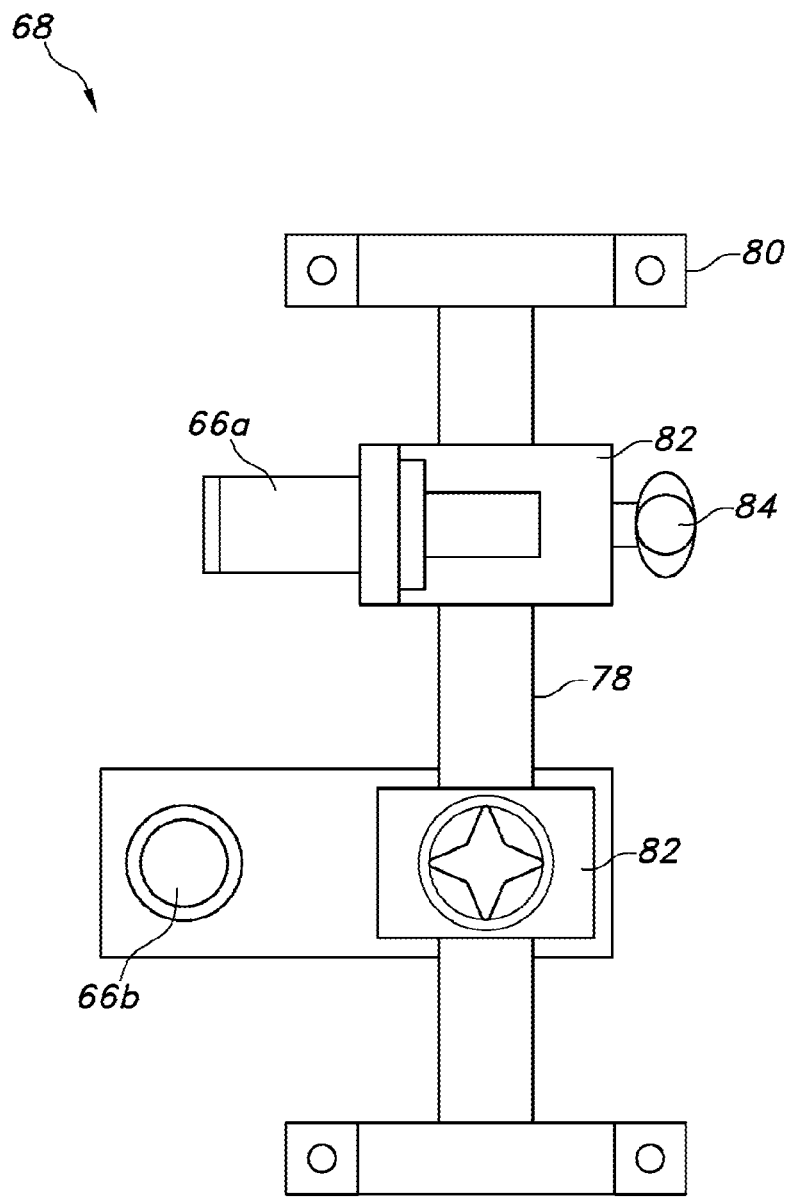
FIG. 7 shows one of the adjustable bracket assemblies of FIGS. 3, 4 and 5 in isolation.

Turning now to FIG. 7, one of the adjustable bracket assemblies 68 is shown in isolation. The bracket assembly 68 generally includes a longitudinal rail 78 mounted to the support frame 32 with mounting brackets 80 attached to the rail at its opposite ends. The rail 78 preferably has a circular cross-section to enable rotational pivoting of the sensors 66a, 66b about the center axis of the rail. The sensors 66a, 66b are attached to the rail 78 via respective carriages 82. The carriages 82 are slidable along the length of the rail 78 and are also rotationally pivotable about the rail so that product vessels 40 having different heights and diameters can be accommodated.

To accomplish such movement, the carriages 82 may take the form of a box-shaped member defining an interior channel for receiving the rail. A clamping device 84, such as a thumb crew, is provided on one of the walls of the box member for securing the carriage in a desired position. In this manner, a sensor 66a can be secured at a desired height with respect to the product vessel to sense whether the liquid in the vessel is at or below the desired height. Alternatively, a sensor 66 b can be rotated towards the panel in a storage position when not in use, as shown at the bottom of FIG. 7.

The present invention provides a system that can conduct more than one automated TFF processes with one control system 36 managing the overall processes. The support frame 32 is designed with multiple stations to support the multiple systems 34 in a manner so as to minimize the overall foot print of the apparatus to condense the parallel processes. While FIG. 3 shows five (5) parallel stations, it is conceivable that more or less stations can be provided.

As described above, each system 34 has a pump 46 that can control flow rate. The pump 46 is preferably contained within an interior of the frame 32 with the necessary fluid connections accomplished via suitable connectors mounted on the pump or in the case of some, like the peristaltic, tubing is routed directly through the pump.

As further described above, each system 34 includes an inlet pressure sensor 64a, a retentate pressure sensor 64b, an optional filtrate pressure sensor 64c (all used to calculate TMP), a vessel 40, an upper liquid level sensor 66a, a lower liquid level sensor 66b, an air in tube detector 56, (to indicate when product and/or buffers have been exhausted during a diafiltration step), a diafiltration valve 58, (that enables a gravity feed of the product or buffer via feedback from the level sensors), a buffer selection valve 52 (that prevents liquid flow from a product or buffer container 38, 39 during a first diafiltration, but opens to introduce a $2^{nd}$ liquid during the $2^{nd}$ diafiltration), a throttle valve 62, (that can throttle down on the process tubing to create a specified TMP), a filtrate scale 69 (e.g., a load cell), and stirrer 70 that can be operated manually or turned on/off by the system.

The singular control system 36 can control the parallel processes simultaneously, and each system 34 can also be operated independently. Each station has its own pressure alarms for minimum and maximum pressure that will stop its pump while other pumps may continue to run.

Thus, various automated process options (recipes) can be performed. For example, in a simple Concentration process, filtrate is removed from the product fluid to provide an end solution having a desired concentration of product in a desired reduced volume. In a Diafiltration process, a desired chemical solution of a product fluid is achieved by adding a buffer. In addition, various combinations of these two processing steps (e.g., Concentration/Diafiltration/Concentration, and Diafiltration1/Concentration1/Diafiltration2/Concentration2) can be achieved in an automated manner. And any of these can be operated concurrently on the different stations.

Diafiltration points are maintained by the liquid level sensors 66a, 66b. The endpoints of the Diafiltration process can be determined by air detected in the tube when that feed is exhausted (by the air in tube detector 56) or a filtrate scale setpoint which determines the amount of buffer used during the diafiltration steps (typically calculated by diafiltration volumes required). Concentration points can be determined by a liquid level sensor 66b or by the filtrate scale setpoint because the control system can measure the increase in scale weight from the start of the concentration step as the amount of liquid removed to yield the final vessel volume target which determines the concentration point.

To program the automated steps for each station, the level sensor positions are set by sliding the mounting carriage 82 holding the selected level sensor 66a, 66b up and down the post 78 and also swiveling it away from the vessel 40. When the sensor 66a, 66b is at the desired level, the clamping device 84 is tightened to keep the sensor in place on the post and in close contact with the vessel. Thus, different size vessels 40 of different heights and diameters can be accommodated by the feature of sliding the level sensor 66a, 66b up/down vertically and also swiveling it horizontally.

In a typical process according to the present invention, a recipe is selected by setting the diafiltration and/or concentration endpoints, the TMP set point and the pump flow rate. The TMP setpoint is controlled by the tubing throttle valve 62. Buffers and product, for feeding to one or multiple stations, are suspended on the support frame 32 for gravity feed to the vessels 40, which is controlled by the diafiltration valve 58.

In the Diafiltration1/Concentration1/Diafiltration2/Concentration2 recipe, the buffer selection valve 52 is closed during the Diafiltration1 step, which allows product or a buffer to be added by the diafiltration valve 58 until it is exhausted and detected by the air in tube detector 56. During the Diafiltration 2 step, the buffer selection valve 52 will open to allow product or a $2^{nd}$ buffer to be added by the diafiltration valve 58 until the end point is reached. The diafiltration valve 58 is an on/off type of valve and the gravity flow rate can be controlled by using the flow restrictor 60 somewhere in the tubing flow path that is selected to limit flow to a specific flow range to optimize the level control of the liquid level sensors 66a, 66b as filtrate leaves the filter 48 to the filtrate scale 69.

In an alternative embodiment of the present invention, one controller 36 can be used to control a series arrangement of more than one TFF process 34 in a completely automated fashion where the liquid flow inputs and outputs of one station can be connected to another station to create a more continuous type of process such as a continuous diafiltration process. Other interconnected process designs of this nature, where one controller with a remote control feature from one graphical user interface, can further streamline set up, monitoring, data collection and analysis.

Other details that are enabled on the one control system for each station include: a filtrate pump (not shown), which is sometimes desired to control the flow through the filter and placed on the filtrate tube; at least one analog input or digital input for expansion of process data collection; a filtrate flow meter to measure filtrate flow (what has gone through the filter) and can also totalize an estimated flow through the filter and with this feature, it could be a substitute for the filtrate scale.

In other embodiments, a diafiltration pump (not shown) could be used as a substitute for the diafiltration valve 58. The pump is controlled by the system to control the vessel level by the level sensors. The analog inputs can be used to connect a separate signal transmitter from a device that is measuring a process fluid property such as pH, dissolved oxygen, conductivity, UV-VIS-NIR absorbance, fluorescence, turbidity concentration, flow, and temperature. Certain measurement instruments are equipped with an analog transmitter feature such as a 4-20 mA analog current signal that can be readily input to the control system. The same instruments measuring fluid properties may feature digital communication such as RS232, RS485 and Ethernet implementing proprietary or Modbus protocols can be readily input to the control system. Both the analog and digital signals can be configured in the control system software to be properly read and spanned so the display the correct process value.

It should be apparent to those skilled in the art that the described embodiments of the present invention provided herein are illustrative only and not limiting, having been presented by way of example only. As described herein, all features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. While various embodiments of the present invention are specifically illustrated and/or described herein, it will be appreciated that modifications and variations of the present invention may be effected by those skilled in the art without departing from the spirit and intended scope of the invention.

All documents, patents and other literature referred to herein are incorporated by reference in their entirety.

The term "comprising" as may be used in the following claims is an open-ended transitional term that is intended to include additional elements not specifically recited in the claims. The term "consisting essentially of" as may be used in the following claims is a partially closed transitional phrase and is intended to include the recited elements plus any unspecified elements that do not materially affect the basic and novel characteristics of the claims. For example, the cable tie may be embossed or printed with indicia and still be included in the meaning of "consisting essentially of", even if not specifically recited. The term "consisting of" as may be used in the following claims is intended to indicate that the claims are restricted to the recited elements.

It should be noted that it is envisioned that any feature, element or limitation that is positively identified in this document may also be specifically excluded as a feature, element or limitation of an embodiment of the present invention.

What is claimed is:

1. A method for performing multiple tangential flow filtration (TFF) processes, the method comprising:
   supporting a plurality of tangential flow filtration (TFF) systems on a single support frame, each of the tangential flow filtration systems comprising a product vessel, a tangential flow filtration (TFF) filter and a pump for circulating a flow of liquid between said product vessel and said filter; and
   controlling said plurality of tangential flow filtration systems with a single electrical controller, wherein the method is used as part of diafiltration process during which liquid or buffer is added to the product vessel to maintain a relatively constant volume as filtrate removal occurs, using a buffer container, containing a liquid to be added to the product vessel in order to change a solvent environment of the product during a diafiltration process, whereby either a single buffer container is connected to multiple TFF systems, or each system comprises its own buffer container; wherein each TFF system has level sensors for detecting a liquid level in its respective product vessel and an air-in-tube detector and the method includes maintaining diafiltration points using the level sensors and detecting air in a tube downstream of a Y-connector connecting tubes from the product and the buffer containers to said tube feeding the product vessel when that feed to the product vessel is exhausted using the air-in-tube detector to determine diafiltration endpoints.

2. The method as defined in claim 1, further comprising:
   in each of the tangential flow filtration systems, detecting air in tubing fluidly connecting a product container to the product vessel of the respective TFF system; and
   closing at least one of a buffer selection valve, fluidly connected to a buffer container and said product vessel, or a diafiltration valve, fluidly connected between said product container and said product vessel, upon said detection of air in said tubing.

3. The method as defined in claim 1, further comprising:
   in each of the tangential flow filtration systems, detecting a level of liquid in the product vessel of the respective TFF system with at least one liquid level sensor; and
   closing at least one of a buffer selection valve, fluidly connected to a buffer container and the product vessel of the respective TFF system, or a diafiltration valve, fluidly connected between said buffer container and the product vessel of the respective TFF system, upon detection of a desired level of liquid in the product vessel of the respective TFF system.

4. The method as defined in claim 1, further comprising:
   in each of the tangential flow filtration systems, detecting an amount of liquid in a filtrate vessel fluidly connected to an outlet of said tangential flow filtration filter with a filtrate scale; and
   closing at least one of a buffer selection valve, fluidly connected to a buffer container and the product vessel of the respective TFF system, or a diafiltration valve, fluidly connected between said buffer container and said product vessel, upon detection of a desired level of liquid in the product vessel of the respective TFF system.

5. The method as defined in claim 1, further comprising in each of the tangential flow filtration systems, controlling average transmembrane fluid pressure in said TFF filter with a throttle valve fluidly connected to an output of said tangential flow filtration filter, said throttle valve applying a back pressure in the TFF filter of the respective TFF system.

6. The method as defined in claim 1, further comprising in each of the tangential flow filtration systems applying a back pressure in said TFF filter with a throttle valve upon detection of an inlet pressure set point.

7. The method as defined in claim 1, further comprising in each of the tangential flow filtration systems applying a back pressure in said filter with a throttle valve upon detection of a retentate pressure set point.

8. The method as defined in claim 1, wherein the support frame defines a plurality of stations for supporting the individual TFF systems, whereby each station has its own pressure alarms for minimum and maximum pressure that will stop its pump while other pumps continue to run.

9. The method as defined in claim 1, used as part of a TFF concentration process, whereby filtrate is removed such that the product vessel contents are concentrated including determining concentration points by using either a level sensor or a filtrate scale setpoint, whereby, if the filtrate scale setpoint is used the concentration points are determined using the final product vessel volume target and the amount of liquid which need to be removed to reach this target, whereby the amount of liquid removed is measured as the increase in scale weight from the start of the concentration process, whereby, if the concentration points are determined by the level sensor, each TFF system has level sensors for detecting a liquid level in its respective product vessel.

10. The method as defined in claim 1, including detecting air in tubing fluidly connecting a product container to said product vessel.

* * * * *